(12) United States Patent
Masciola

(10) Patent No.: US 12,104,573 B2
(45) Date of Patent: Oct. 1, 2024

(54) REPOSITIONING A FLOATING OFFSHORE WIND TURBINE

(71) Applicant: Siemens Gamesa Renewable Energy A/S, Brande (DK)

(72) Inventor: Marco Masciola, Louisville, CO (US)

(73) Assignee: SIEMENS GAMESA RENEWABLE ENERGY A/S, Brande (DK)

( * ) Notice: Subject to any disclaimer, the term of this patent is extended or adjusted under 35 U.S.C. 154(b) by 0 days.

(21) Appl. No.: 18/032,625

(22) PCT Filed: Oct. 14, 2021

(86) PCT No.: PCT/EP2021/078529
§ 371 (c)(1),
(2) Date: Apr. 19, 2023

(87) PCT Pub. No.: WO2022/089957
PCT Pub. Date: May 5, 2022

(65) Prior Publication Data
US 2023/0407846 A1    Dec. 21, 2023

(30) Foreign Application Priority Data
Oct. 26, 2020    (EP) .................................... 20203860

(51) Int. Cl.
*F03D 13/25*    (2016.01)
*F03D 13/40*    (2016.01)

(52) U.S. Cl.
CPC ........... *F03D 13/40* (2016.05); *F03D 13/256* (2023.08); *F05B 2240/93* (2013.01);
(Continued)

(58) Field of Classification Search
CPC .... F03D 13/40; F03D 13/256; F05B 2240/93; F05B 2240/95; F05B 2260/02; F05B 2260/84
See application file for complete search history.

(56) References Cited

U.S. PATENT DOCUMENTS 9,670,908 B2    6/2017    Dupin De La Gueriviere
2010/0283246 A1*    11/2010    Christensen .......... F03D 7/0272
290/44
(Continued)

FOREIGN PATENT DOCUMENTS

DK    201470456 A1    5/2015
EP    2267297 B1 *    8/2017    ............. B63B 21/50
(Continued)

OTHER PUBLICATIONS

Schreiber, J. et al: "Wind shear estimation and wake detection by rotor loads—First wind tunnel verification"; Journal of Physics: Conference Series; vol. 753; Sep. 1, 2016; pp. 032027; XP055794131; GB ISSN: 1742-6588; DOI: 10.1088/1742-6596/753/3/032027.
(Continued)

*Primary Examiner* — David E Sosnowski
*Assistant Examiner* — Theodore C Ribadeneyra
(74) *Attorney, Agent, or Firm* — Schmeiser, Olsen & Watts LLP

(57) ABSTRACT

A method of repositioning a floating offshore wind turbine located at a current offshore position and having rotor blades rotating in a rotor blade plane includes: measuring a first value of a variability of a load related to a first location at the wind turbine; measuring a second value of a variability of a load related to a second location at the wind turbine; comparing the first value with the second value; and moving the wind turbine along a direction depending on the comparison and in particular further depending on the first location relative to the second location.

15 Claims, 3 Drawing Sheets

Figure 3:
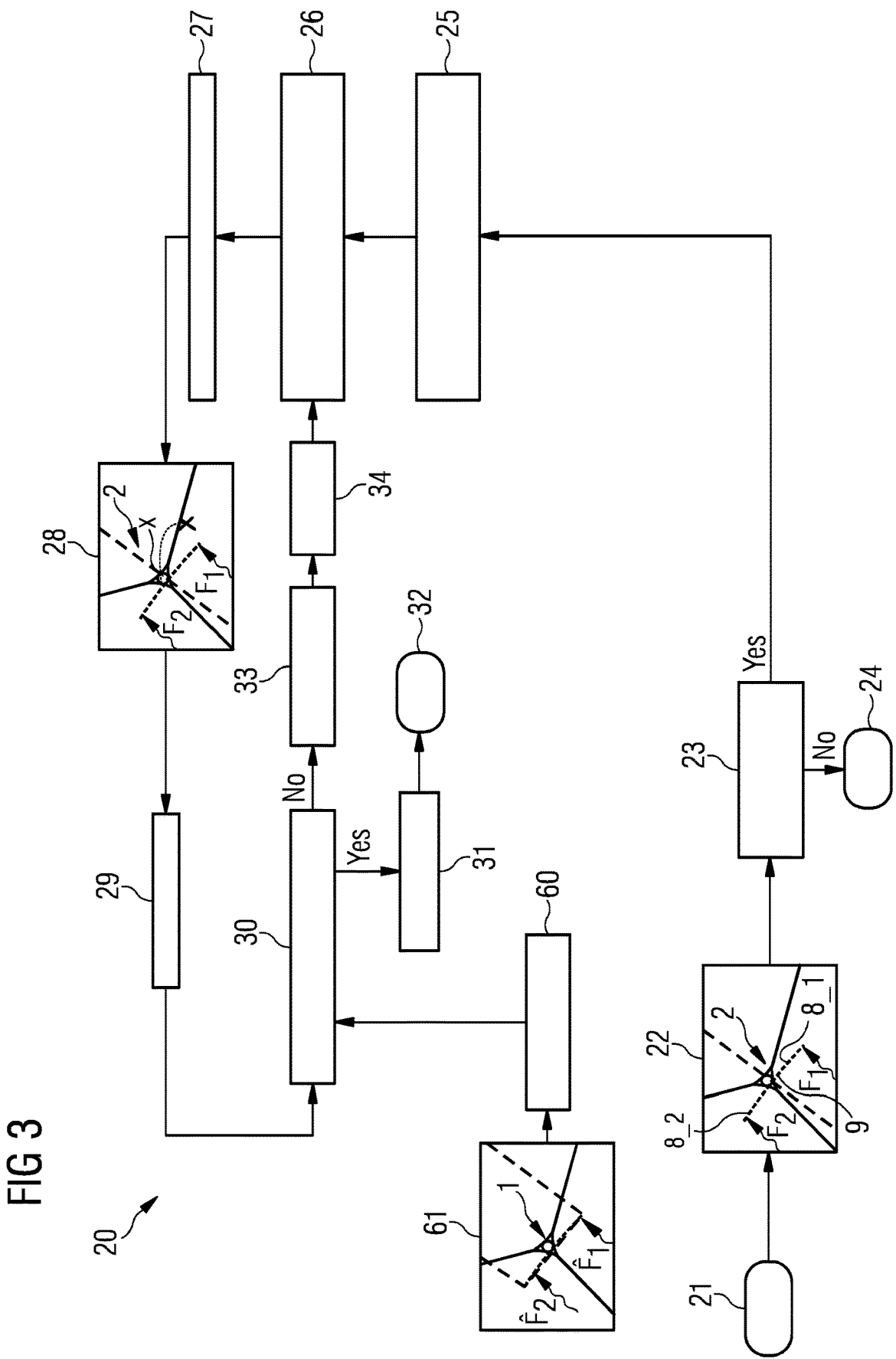

(52) U.S. Cl.
CPC ....... *F05B 2240/95* (2013.01); *F05B 2260/02* (2013.01); *F05B 2260/84* (2013.01)

(56) References Cited

U.S. PATENT DOCUMENTS

| | | |
|---|---|---|
| 2011/0074155 A1 | 3/2011 | Scholte-Wassink |
| 2011/0164975 A1* | 7/2011 | Vyas ................... F03D 1/0608 416/37 |
| 2012/0091713 A1* | 4/2012 | Egedal .................. F03D 7/042 290/44 |
| 2015/0167637 A1* | 6/2015 | Kooijman ................ F03D 7/02 416/61 |
| 2022/0412313 A1* | 12/2022 | Post ....................... F03D 17/00 |

FOREIGN PATENT DOCUMENTS

| | | |
|---|---|---|
| FR | 3011813 A1 | 4/2015 |
| JP | 6414837 B2 | 10/2018 |
| WO | WO 2019243152 A1 | 12/2019 |

OTHER PUBLICATIONS

Cacciola, S. et al: "Wake center position tracking using downstream wind turbine hub loads"; Journal of Physics: Conference Series; vol. 753; Sep. 1, 2016; pp. 032036; XP055658107; GB ISSN: 1742-6588; DOI: 10.1088/1742-6596/753/3/032036.

* cited by examiner

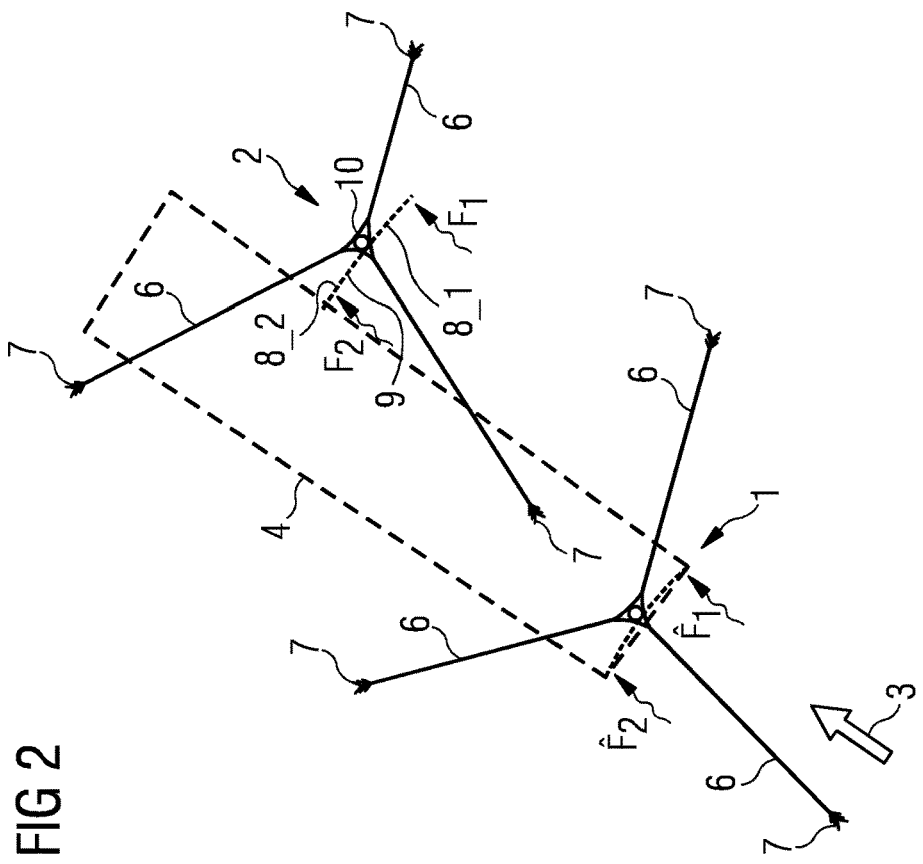
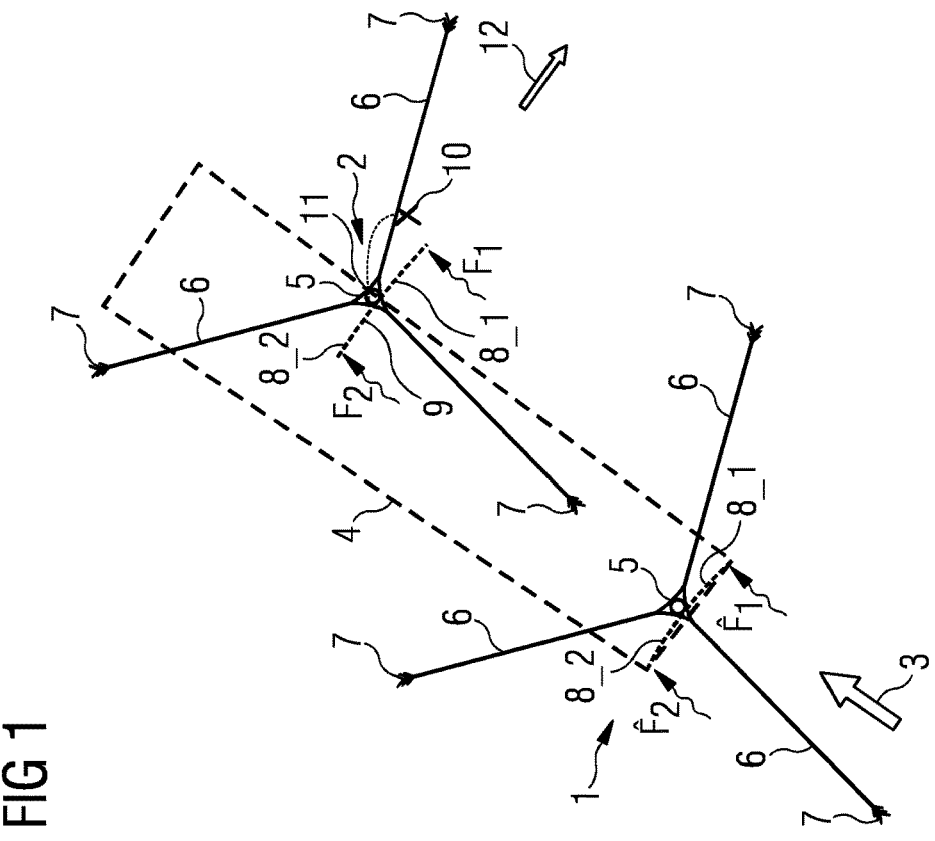

REPOSITIONING A FLOATING OFFSHORE WIND TURBINE

This application claims priority to PCT Application No. PCT/EP2021/078529, having a filing date of Oct. 14, 2021, which claims priority to EP Application No. 20203860.0, having a filing date of Oct. 26, 2020, the entire contents both of which are hereby incorporated by reference.

FIELD OF TECHNOLOGY

The following relates to a method and to an arrangement of repositioning a floating offshore wind turbine located at a current offshore position and having rotor blades rotating in a rotor blade plane. Furthermore, the following relates to a wind turbine comprising the arrangement.

BACKGROUND

Nowadays, many wind turbines are installed offshore due to better wind conditions compared to onshore wind conditions. These floating offshore wind turbines (FOWT) are installed at floating platforms floating on the sea. The FOWTs experience environmental disturbances originating from many sources. These disturbances may lead to degradation or damage in the machine mechanical fatigue performance. The presence of wake-induced turbulence and vortex-induced vibrations (VIV) in turn may contribute to unfavourable secondary loads by virtue of the wind farm layout and proximity to adjacent units. These disturbances tend to diminish as 1) the distance between FOWT units increases and/or 2) upstream FOWT units avoid shadowing the downstream wind turbines. In practice, space between FOWT units is limited by the wind farm lease area size and minimum number of units required to make the farm economically viable. Therefore, large spacings or distances between wind turbine units is not a practical solution.

The floating wind industry is still in the formative stage and technology specifically addressing the FOWT challenges indicated above are still in a "discovery" phase. The conventionally widely accepted practice to mitigate wake-interference uses active control to offset the rotor yaw angle and deliberately produce a yaw error. While this approach is favourable for bottom-founded wind turbines, a deliberate yaw offset can lead to a host of other issues and problems for the FOWTs. Therefore, FOWTs will require adoption of new technologies to mitigate wake-interference with the farm.

U.S. Pat. No. 9,670,908 B2 discloses a wind farm including a control unit and a plurality of floating platforms, each of which is anchored to at least one anchor point and includes a shift device for shifting the wind turbine as a function of a set of parameters, including wind direction, in order to minimize aerodynamic wake effects. A control unit contains a table of predefined positions for maximizing power generation. Furthermore, a set of sensors provide wind direction information. An actuator is adapted for pulling on an anchor line in order to shift the wind turbine. The document addresses to maximize power production by reducing exposure to wake-induced turbulence. Thereby, a table of predefined positions for maximizing power generation seems to be required.

The document US 2011/0074155 A1 discloses a floating offshore wind farm comprising a positioning system adapted to determine a horizontal position of the first wind turbine relative to the second wind turbine and a drive system adapted to horizontally move the first wind turbine relative to the second wind turbine. A first operational status of the first wind turbine and a second operational status of the second wind turbine is received and a new horizontal position of the first wind turbine is determined such that the mechanical load of the first wind turbine and/or the second wind turbine is decreased when the first wind turbine is at the new horizontal position.

The conventionally known methods and systems do not in all situations or circumstances ensure that fatigue load or fatigue damage on an offshore wind turbine is mitigated or even avoided. Furthermore, conventionally known methods and systems are complex and often require geometrical presentations or considerations of the environment. Furthermore, some of the conventionally known techniques may rely on monitoring electrical power output. However, power output not necessarily is an optimal parameter to ensure mitigating fatigue load or fatigue damage. Furthermore, often, cross communication of position information between adjacent FOWT units may conventionally be required thereby increasing complexity of the system and method. Furthermore, conventionally, complex wake interaction models may be required, for example an estimate of an aerodynamic influence between wind turbine units. Thereby, often, complex physical mathematical modelling is required.

Thus, there may be a need for a method and a corresponding arrangement of repositioning a floating offshore wind turbine, wherein in particular fatigue damage or fatigue load may be reduced and in general mechanical load may be reduced during operation.

SUMMARY

According to an embodiment of the present invention it is provided a method of repositioning a floating offshore wind turbine located at a current offshore position and having rotor blades rotating in a rotor blade plane, the method comprising measuring a first value of a variability of a load related to a first location at the wind turbine; measuring a second value of a variability of a load related to a second location at the wind turbine; comparing the first value with the second value; and moving the wind turbine along a (e.g. horizontal) direction depending on the comparison and in particular further depending on the first location relative to the second location.

The method may partly be implemented in hardware and/or software. The method may for example be performed by a wind turbine controller or a wind farm controller. The considered wind turbine may be one of plural wind turbines of an offshore wind park.

The variability of the load may (for the first location as well as the second location) be related or caused by the wind turbulence at the different locations. The wind turbulence may for example be related to a variability or a standard deviation of the wind speed at the first location and the second location, respectively. The turbulence may for example be due to wake effects as caused by one or more upstream wind turbines, i.e., wind turbines which are upstream relative to the considered wind turbine, wherein upstream means relative to the present wind direction.

The load may for example be measured by one or more sensors as will be explained further below. The method considers the variability of the load thus being a parameter which measures or is indicative of to what degree the load varies with time. Therefore, in order to derive the variability of the load, plural load measurements may be considered. For example, a sensor may sample load measurements at a relatively small or fine difference time interval. The time window over which the load measurements are considered may for example range between 120 seconds and 600 seconds. The sampling time interval of the load measurements may for example range between 120 seconds and 600 seconds.

The first location at the wind turbine may be apart from the second location of the wind turbine by between 10 m and 100 m for example. Thus, the method may consider variabilities of the load as determined for two different locations which may experience different wind conditions, in particular regarding turbulence. If the variabilities of the load at the different locations are very different, then it may indicate that at least a portion of the wind turbine is in a high turbulence region. This high turbulence region may for example be due to wake effects caused by one or more upstream wind turbines. Upon determination of at least one of the locations being located in a potential wake region, the wind turbine may be moved such that the wind turbine leaves the current offshore position. Thereby, primarily or entirely, the power output of the wind turbine or other mechanical power output may not be considered.

The comparison of the first value and the second value (of respective variabilities of the load) related to the first location and the second location, respectively, may be performed in different manners. The variabilities of the load may for example relate to or be the standard deviation of the rotor thrust load.

The movement of the wind turbine may for example be performed depending on which one of the first value or the second value is greater. Furthermore, for moving the wind turbine, the nacelle orientation may be considered. The nacelle orientation is determined using a combination of accelerometer and a global positioning system to determine the position and orientation of the wind turbine, and encoders to determine the relative orientation of the nacelle relative to the flowing unit.

Embodiments of the present invention address wake-induced turbulence and vortex induced vibrations in wind farm layout load by dynamically altering the location of the FOWT units to areas where the disturbances are reduced or even vanish. Thereby, fatigue life of both the wind turbine and the floating foundation may be increased. Thereby, the FOWTs may be connected to the sea floor using flexible cables known as "mooring lines". Those FOWTs have the advantage to be capable to moving away from the upwind disturbances and apply readjustments in seeking a load neutral position.

Embodiments of the present invention provide an apparatus utilizing dynamic positioning to move a FOWT away from the wake or VIV (vortex induced vibrations) produced by an upstream FOWT. Thereby, a controller may be employed to activate the dynamic positioning actions. These method steps may allow the downstream unit to produce the same amount of power as the upstream wind turbine for the same or lower loads. The dynamic positioning may be achieved by synchronizing mooring line pay-in/pay-out and reposition a FOWT to a target location where the turbulence is less severe or where VIV is reduced or minimal.

Embodiments of the present invention may be effective for mitigating loads if 1) turbulent wake effects are present and/or 2) the wind farm comprises two or more FOWT units. Embodiments of the present invention enable the FOWT system to achieve a lower component cost on both the wind turbine and floating foundation by improving fatigue life performance.

According to an embodiment of the present invention, the first location at the wind turbine is arranged in a first lateral half of the wind turbine and the second location at the wind turbine is arranged in a second lateral half of the wind turbine. The first lateral half of the wind turbine and the second lateral half of the wind turbine may be defined as a right half and a left half of the wind turbine when facing the hub viewed along the rotor axis.

According to an embodiment of the present invention, the first location at the wind turbine is arranged in a first lateral half of the rotor blade plane and the second location at the wind turbine is arranged in a second lateral half of the rotor blade plane.

The rotor blade plane may be considered as a plane perpendicular to the main rotor shaft at which the rotor blades are mounted. During operation while the rotor is rotating, the rotor blades may occupy essentially a plane disk having a circular shape. The rotor blade plane may be one plane in the disk, for example a plane in which one or more sensors, such as strain sensors, are installed at the one or more rotor blades. At least one sensor may be required in order to measure the load related to the first location as well as the load related to the second location. The load related to the first location may for example be measured during a first time interval in which the respective sensor is arranged within the first lateral half of the rotor blade plane. The load related to the second location may be for example measured during a second time interval, during which the sensor is located within the second lateral half of the rotor blade plane. In other embodiments, more than one sensor may be employed for measuring the load related to the first location and the load related to the second location, respectively. Sensors may for example also be installed at the nacelle to measure the rotor rotational speed, the mechanical power generated, and the blade pitch angle. The combination of the three sensor inputs would then estimate the thrust load across the rotor area. This thrust load estimate is related to the used algorithm for estimating wind speed from the same sensor inputs. A coordinate transforms is then performed to calculate the load distribution on each blade to determine the time varying thrust force on each rotor area lateral half.

Having the first location in the first lateral half and the second location in the second lateral half of the rotor blade plane may allow to determine whether the variabilities of the loads in the different areas are in fact different and may reliably indicate whether a portion of the wind turbine is potentially in a wake area or wake condition. Thereupon, moving away the wind turbine from the current offshore position may advantageously be initiated.

According to an embodiment of the present invention, the direction comprises a lateral direction, the method further comprising determining the lateral, in particular horizontal, direction to point from a center area of the rotor blade plane to the first lateral half, if the first value is smaller than the second value, to point from a center area of the rotor blade plane to the second lateral half, if the second value is smaller than the first value.

The movement of the wind turbine is in the horizontal direction on the surface of the sea. The lateral direction is determined based on the comparison of the first value and the second value. Thereby, a simple method for determining the lateral direction is provided. For this method step, also any statistical model may not necessarily be required. The determined lateral direction may be perpendicular to the rotor axis direction. Thus, the lateral direction may be depending on the nacelle orientation.

According to an embodiment of the present invention, comparing the first value with the second value comprises assessing whether an absolute value of a difference between the first value and the second value is greater than a threshold and moving the wind turbine comprises to move the wind turbine only if the absolute value of the difference is greater than a threshold.

Thereby, a simple prescription to compare the different values is provided. The threshold may be defined depending on the particular application. For example, experimental results may be considered for defining the threshold. If the wind turbine is only moved if the absolute value of the difference is greater than a threshold, unnecessary movements of the wind turbines may be avoided. Furthermore, as a criterion to move the wind turbine, it may be defined that the absolute value of the difference is greater than a threshold for longer than a threshold time interval.

According to an embodiment of the present invention, the variability of the load is indicative of a variance or a standard deviation of load sensor measurements of at least one sensor installed at the wind turbine, the sensor comprising the aforementioned nacelle sensors and/or strain sensor and/or fibre Bragg sensor installed at nacelle and/or a rotor blade, wherein the variability of the load is in particular indicative of a turbulence of wind impacting at the wind turbine, in particular at least one rotor blade.

Thereby, conventionally available sensors may be employed in embodiments of the present invention. The standard deviation may relate to a conventionally known statistical standard deviation. The standard deviation may advantageously be indicative of the turbulence of wind impacting on the blade or the nacelle. Conventionally, turbulence of wind may lead to fatigue damage or increase fatigue load. Thereby, fatigue damage or fatigue load may be reduced in embodiments of the present invention.

According to an embodiment of the present invention, the wind turbine is situated on a floating platform, wherein moving the wind turbine comprises controlling a positioning apparatus configured to change the offshore position of the wind turbine, the positioning apparatus comprising at least one actuator arranged at the floating platform and/or at the sea ground and/or in the sea, wherein the positioning apparatus in particular comprises at least two mooring lines being connected at one end to different locations at the floating platform and connected at another end to different location of a sea ground, the actuator being configured to loosen and tighten the mooring lines.

Thus, the floating platform is not fixedly connected to the sea ground but is movable in the horizontal direction. Thereby, the advantage is provided that load, in particular fatigue damage may be decreased and/or power production may be increased. The actuator may for example comprise an electric motor and/or hydraulic system. By also supporting mooring lines, a conventionally available positioning apparatus may be supported.

According to an embodiment of the present invention, the method further comprises employing a first statistical model, in particular Bayesian model, relating a wake affected state to at least one of: the offshore position of the wind turbine; an orientation of the nacelle of the wind turbine, the nacelle at least partly harbouring the rotor; variabilities of load measurement values, in particular times series; positioning apparatus control inputs, in particular pay-in and/or pay-out length of mooring lines, in particular time series; a wind speed, in particular time series; a wind direction.

For example, the first statistical model may provide the (conditional) probability that the wind turbine is in a wake region or is not in a wake region depending on the parameters as listed above. The statistical model may have been derived from previously acquired training data measuring or determining all of the above parameters or at least monitoring a portion of the above listed parameters. The load measurement values may for example comprise load measurement values relating to the first position and/or the second position.

The load measurement values may continuously be monitored and may relate to any location in between the first and second location.

Using the first statistical model it may be enabled to determine the (conditional) probability that the wind turbine is in a wake affected state or not given the other above listed parameters.

According to an embodiment of the present invention, the method further comprises employing a second statistical model, in particular Bayesian model, relating the offshore position of the wind turbine to at least one of: a wake affected state; an orientation of the nacelle of the wind turbine, the nacelle at least partly harbouring the rotor; variabilities of load measurements values, in particular times series; positioning apparatus control inputs, in particular pay-in or pay-out length of mooring lines, in particular time series; a wind speed, in particular time series, a wind direction, wherein the first model and the second model are in particular derivable from essentially same training data.

Utilizing the second statistical model may enable to in particular determine a target offshore position given one or more of the parameters as listed above. Thereby, an optimization method may for example be performed. Embodiments of the present invention adopt tensegrity architecture principles by applying tension on mooring lines to navigate the floating platform to an optimal position. The optimal position may be a location, where the mechanical thrust load standard deviations are balanced across the rotor area. Thereby, the wind turbine may be repositioned to draw it away from the upwind wakes and VIV interference. Thereby, simultaneous localization and mapping (SLAM) may be adapted to evade the need for an explicit mathematical description of the terrain geometry of for example wake interference zone and the wind turbine kinematics model.

The first statistical model may define the conditional probability of a wind turbine not being in a wake zone. The first statistical model may describe or define the probability of the wind turbine being in a wake zone or not being in a wake zone given the wind turbine kinematic state, the load measurements and positioning apparatus controller inputs.

The second statistical model may be utilized to solve the first statistical model for determining the environmental mapping m_i (i.e., being in a wake region or not being in a wake region) and the trajectory planning x_i.

According to an embodiment of the present invention, the method further comprises determining a target offshore position based on the first and/or the second statistical model; and moving the wind turbine to the target offshore position. Thereby, not only the moving direction is defined but also the final desired target offshore position. Thereby, it may be enabled to move the wind turbine into a new offshore position which to a higher degree of reliability is in an acceptable position, i.e., in a wake-free area.

According to an embodiment of the present invention, the method further comprises determining a trajectory from the current offshore position to the target offshore position based on the first and/or the second statistical model and moving the wind turbine to the target offshore position along the determined trajectory.

Determining the trajectory may utilize or employ the first statistical model and/or the second statistical model. When the trajectory is also determined, it may for example be avoided that the wind turbine platform collides with one or more other platforms. Further restrictions may be considered for determining the trajectory. Therefore, the movement may be improved, in particular increasing safety.

According to an embodiment of the present invention, the method further comprises, when the wind turbine is at the target offshore position or at any intermediate offshore position, measuring another first value of a variability of the load related to the first location at the wind turbine; measuring another second value of a variability of the load related to the second location at the wind turbine and in particular substantially simultaneously or at least substantially same wind condition measuring a first reference value of a variability of a load related to a first location at a reference wind turbine; measuring a second reference value of a variability of a load related to a second location at the reference wind; comparing the other first value with the first reference value; comparing the other second value with the second reference value; and determining that the wind turbine is at an acceptable offshore position, in particular outside a wake region, based on the reference comparisons.

According to this embodiment it may be determined whether the repositioned wind turbine experiences similar variability of load as the reference wind turbine, wherein the reference wind turbine may represent a wind turbine which is essentially not obstructed by any barriers or other wind turbines regarding wind interaction. The reference wind turbine may for example be considered as an unwaked wind turbine. Thereby, a reliable measure is provided enabling to accurately determine whether the target offshore position is in fact at an acceptable offshore position. The other first value and the other second value may for example be determined utilizing the same or other sensor(s) as were used for determining the first value and the second value, respectively. For the reference wind turbine, similar or same types of sensors may be utilized as have been utilized for measuring the respective values for the considered wind turbine to be repositioned. In particular, for the variabilities, the standard deviations may be determined of the load values as measured at the respective different locations.

According to an embodiment of the present invention, the reference wind turbine is located not more than 5 km (or 7 km or 10 km) away from the considered wind turbine and/or wind impacting onto the reference wind turbine is unobstructed from any other wind turbine, and in particular further comprising updating the first and/or the second statistical model based on the reference comparisons.

Thereby, the reference wind turbine may represent a wind turbine experiencing wind impact which is not disturbed by any other upwind barriers, such as other wind turbines. If the wind turbine considered for repositioning which has been repositioned shows or exhibits similar variabilities of the loads at the different locations as the reference wind turbine, this may reliably indicate that also the repositioned wind turbine is now in an essentially wake-free area and thereby experiencing wind conditions similar as the reference wind turbine.

Furthermore advantageously, the statistical models may be updated utilizing the assessment based on the reference comparison. Thereby, the statistical models may be improved and will incrementally improve.

According to an embodiment of the present invention, comparing the other first value with the first reference value comprises to determine a first absolute value of a difference between the other first value and the first reference value; wherein comparing the other second value with the second reference value comprises to determine a second absolute value of a difference between the other second value and the second reference value; wherein determining that the wind turbine is at an acceptable offshore position comprises to determine that a sum of the first absolute value and the second absolute value is smaller than a reference threshold.

Thereby, a simple manner for performing the reference comparisons is provided. The reference threshold may be determined depending on the application, sensitivity and specificity. If the sum of the first absolute value and the second absolute value is not smaller than the reference threshold, it may indicate, that the repositioned wind turbine is not at an acceptable offshore position, is in particular in an at least partially waked area or offshore position.

It should be understood, that features, individually or in any combination, disclosed, described, explained or provided for a method of repositioning a floating offshore wind turbine are also, individually or in any combination, applicable to an arrangement for repositioning a floating offshore wind turbine according to embodiments of the present invention and vice versa.

According to an embodiment of the present invention it is provided an arrangement for repositioning a floating offshore wind turbine located at a current offshore position and having rotor blades rotating in a rotor blade plane area, the arrangement comprising a processor. The processor is adapted to receive a first value of a variability of a load related to a first location at the wind turbine and to receive a second value of a variability of the load related to a second location at the wind turbine; to compare the first value with the second value; and to derive control signals adapted to move the wind turbine along a direction depending on the comparison and in particular further depending on the first location relative to the second location.

The arrangement may further comprise at least one sensor capable of providing measurement signals of a load at least the first and/or second location. Furthermore, the arrangement may also comprise a positioning apparatus.

According to an embodiment of the present invention it is provided a wind turbine, comprising: a rotor at which plural rotor blades are mounted and allowed to rotate in a rotor blade plane; at least one sensor adapted to measure plural first load values of a load related to a first location at the wind turbine and to measure plural second load values of the load related to a second location at the wind turbine; an arrangement according to the preceding embodiment communicatively coupled to the sensor in order to receive measurement values, in particular a positioning apparatus configured to change the offshore position of the wind turbine and communicatively coupled to the processor in order to receive control signals.

The aspects defined above and further aspects of embodiments of the present invention are apparent from the examples of embodiment to be described hereinafter and are explained with reference to the examples of embodiment. Embodiments of the invention will be described in more detail hereinafter with reference to examples of embodiments but to which the invention is not limited.

BRIEF DESCRIPTION

Figure 4:
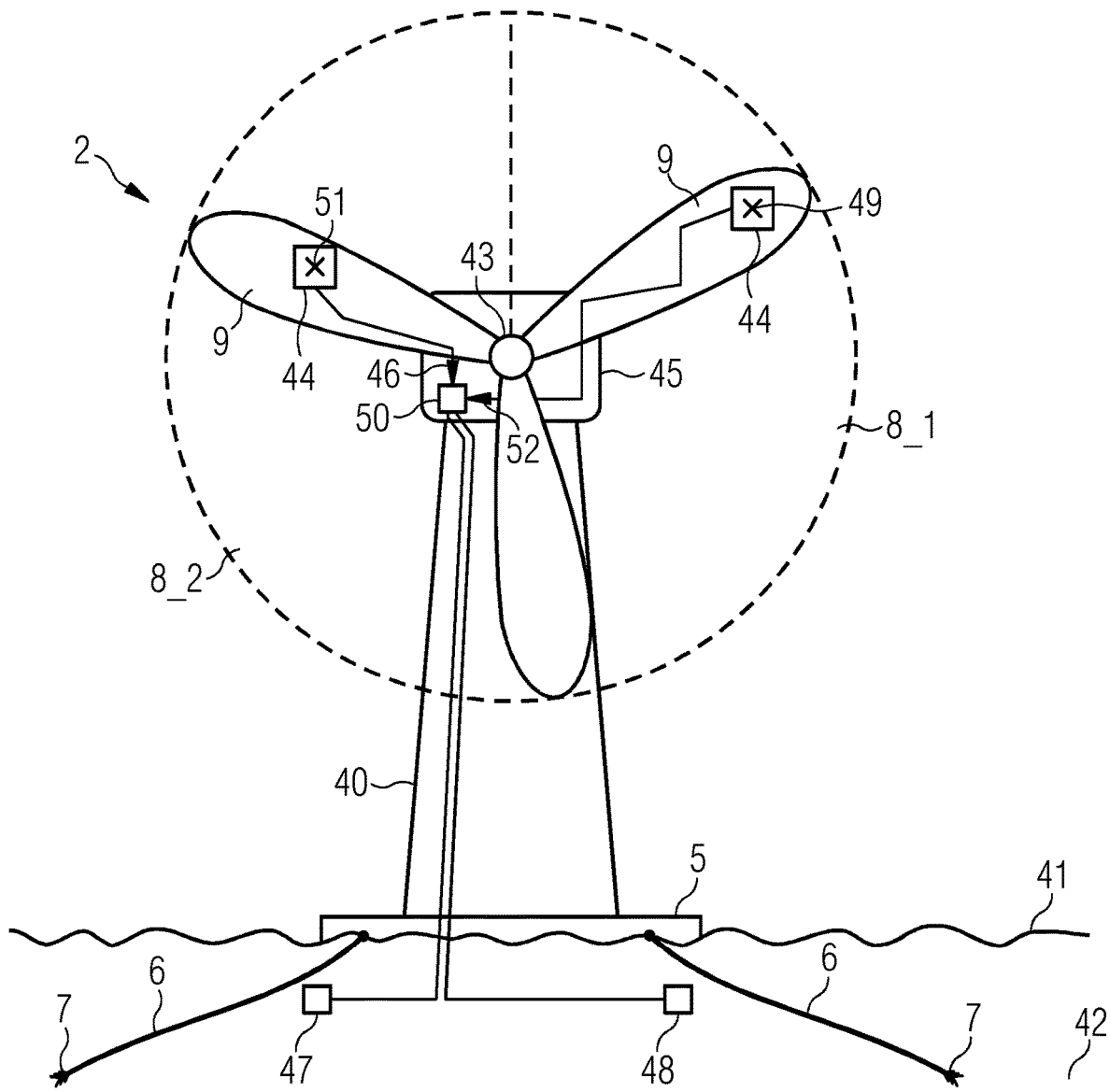

Some of the embodiments will be described in detail, with reference to the following figures, wherein like designations denote like members, wherein:

FIG. 1 schematically illustrates a situation during a method according to an embodiment of the present invention;

FIG. 2 schematically illustrates another situation during a method according to an embodiment of the present invention;

FIG. 3 schematically illustrates a method scheme according to an embodiment of the present invention; and FIG. 4 schematically illustrates a wind turbine according to an embodiment of the present invention.

DETAILED DESCRIPTION

FIG. 1 is an elevational view of two offshore wind turbines 1, 2 illustrating a situation during a method of repositioning a floating offshore wind turbine according to an embodiment of the present invention. The arrow 3 indicates a wind direction. Therefore, the wind turbine 1 is an upwind wind turbine potentially influencing the downstream wind turbine 2 due to a wake area as is illustrated in the area 4. It should be noted that the area 4 is an area of wind velocity standard deviation turbulence having an increased value due to the wake-induced interference of the upstream wind turbine 1. This area 4 is introduced for visual demonstration purposes only, but it is not essential for the model/algorithm as disclosed in the present application according to an embodiment of the present invention.

The upwind wind turbine 1 is situated on a floating platform 5 which is connected to mooring lines 6 which are connected at one end to different locations at the floating platform 5 and which are connected at another end to different locations 7 at the sea ground.

Similarly, the downstream wind turbine 2 (considered for repositioning) is arranged on a floating platform 5 which is also connected to mooring lines 6 which are on one end connected to different locations of the floating platform 5 and at other ends connected to different locations at the sea ground 7. By paying-in/paying-out different mooring lines 6, the wind turbine 2 may horizontally be moved which is employed according to embodiments of the present invention.

The upwind wind turbine 1 may serve as a reference wind turbine which is not affected by any further upstream wind turbine regarding impacting wind. The reference wind turbine 1 comprises at least one sensor (as will be illustrated in FIG. 4) which is capable of measuring a load $F\hat{\ }\_1$, $F\hat{\ }\_2$ at different lateral halves of a rotor blade plane 8. The rotor blades 9 rotate within the rotor blade plane 8. The first reference load measurements $F\hat{\ }\_1$ relate to the load measurements in the first lateral half of the rotor blade plane 8 and the reference load measurements FA 2 relate to the load measurements in the second lateral half of the rotor blade plane 8.

Similarly, the wind turbine 2 considered for repositioning also comprises at least one sensor being capable of measuring a load F_1 related to a first half of the rotor blade plane 8. Further, the wind turbine 2 comprises a sensor for measuring a load F_2 related to the load at the second lateral half of the rotor blade plane 8. The rotor blade area is in FIG. 1 separated in a first lateral half 8_1 and a second lateral half 8_2 of the rotor blade plane, collectively labelled with reference sign 8. The sensor of wind turbine 2 may be arranged at any position within either the first lateral half 8_1 or the second lateral half 8_2 of the rotor blade plane or the entire wind turbine 2. The wind turbine 2 comprises an arrangement for repositioning a floating offshore wind turbine which is capable of performing a method of repositioning a floating offshore wind turbine according to an embodiment of the present invention. The arrangement will be described in more detail with reference to FIG. 4 below.

The wind turbine 2 is currently located at current offshore position 11 (X0). During the method of repositioning a floating offshore wind turbine, a target position 10 (X) is determined. This target position X is in particular determined based on comparing variabilities of the loads F_1 and F_2 as measured at different lateral positions of the rotor blade plane 8. Further the heading direction 12 is determined.

In FIG. 2, an elevational view of a next situation is illustrated, wherein the wind turbine 2 has been moved to the target offshore position X which has been determined previously. Thus, the wind turbine 2 is entirely arranged outside the wake area 4. In particular, the entire rotor blade plane, including the first lateral half 8_1 and the second lateral half 8_2, is arranged outside the wake area 4.

FIG. 3 schematically illustrates a method of repositioning a floating offshore wind turbine according to an embodiment of the present invention. The method 20 starts at a starting block 21. In the block 22, load measurements F_1, F_2 are performed at a first lateral half 8_1 and a second lateral half 8_2 of a rotor blade plane spanned by rotating rotor blades 9 of wind turbine 2. From the load measurements F_1, F_2 at the different locations, respective variabilities are determined. Thereby, in the present embodiment, the variabilities are calculated by calculating respective standard deviations σ. Thus, the term σ(F_1) represents a first value of a variability of a load related to a first location at the wind turbine. Similarly, the term σ(F_2) represents a second value of a variability of a load related to a second location at the wind turbine. In the block 23, the first value σ(F_1) is compared with the second value σ(F_2). In particular, the absolute value of a difference between the first value and the second value is determined and assessed whether this difference is greater than a threshold E. Thus, in the box 23, the following evaluation is performed:

$$\in < \sigma(F_2) - \sigma(F_1) \|$$

If the evaluation is logically false, the method terminates at the stop block 24. If the evaluation performed in block 23 is logically true, it is switched to an evaluation block 25. In the evaluation block 25, the following assessments or evaluations are performed for determining moving direction:

if $\sigma(F\_1) < \sigma(F\_2)$ then move right.

if $\sigma(F\_2) < \sigma(F\_1)$ then move left.

Thus, a moving direction is determined based on whether the first value σ(F_1) is smaller or greater than the second value σ(F_2). Thereby, the movement direction is towards that lateral half from the center area of the rotor blade plane for which the respective variability of the load is smaller.

In a subsequent block 26, a first statistical model $P(m_i | x_i, x_{1:i}, u_{1:i})$; and a second statistical model $P(x_i | m_i, z_{1:i}, u_{1:i})$ are considered for solving the trajectory and the environmental map. Thus, thereby, the target offshore position and the trajectory towards the target offshore position are determined.

In one or more steps of module 27 it is incrementally moved towards the target position X, as is also illustrated in block 28. In the block 29, the target position X is reached.

In a subsequent block 30 it is evaluated whether the wind turbine is now at an acceptable offshore location. Thereby, the first value σ(F_1) is compared with a first reference value σ($F\hat{\ }\_1$) and the second value σ(F_2) is compared with a second reference value σ($F\hat{\ }\_2$). The reference values (relating to the "unwaked" wind turbine) are obtained from block 60 receiving data from reference turbine 1 from block 61. In particular, in the evaluation block 30, the following assessment is performed:

$$\|\sigma(\hat{F}_1)-\sigma(F_1)\|+\|\sigma(\hat{F}_2)-\sigma(F_2)\|\le\in_1$$

If the assessment made in block 30 results in a logically true result, it is switched to a method block 31. In the method block 31, the first statistical model and/or the second statistical model are updated. In particular, in block 31, the following assignments are performed:

$$P(m_i|x_i,z_{1:i},u_{1:i})=1$$

$$P(x_i|m_i,z_{1:i},u_{1:i})=1$$

Then the method stops at a stop block 32.

If the assessment done in block 30 results in a logically false result, it is switched to an assignment block 33. Also in this assignment block 33, the first statistical model and/or the second statistical model is updated. In particular, in block 33, the following assignments are performed:

$$P(m_i|x_i,z_{1:i},u_{1:i})=0$$

$$P(x_i|m_i,z_{1:i},u_{1:i})=0$$

In method step 34, an incrementation is performed. This incrementation occurs in between the interval in which a new value for the standard deviation $\sigma(\bullet)$ is computed. Then it is returned to the method block 26 wherein the trajectory and environmental map are solved as previously described.

The Bayesian model $P(m_i|x_i, x_{1:i}, u_{1:i})$ may define the conditional probability that a wind turbine is not in a waked area. Thereby, this equation may describe the probability of m of the environmental map, i.e., wake area, occurring given the inputs x (wind turbine kinematic state), z (load measurements) and u (controller inputs) are true.

Similarly, a Bayesian model $P(x_i|m_i, z_{1:i}, u_{1:i})$ is employed to solve with the one above to determine the environmental mapping m_i and trajectory planning x_i. The function $\sigma(\bullet)$ is the standard deviation determined by deriving the known statistical standard deviation of load measurements as follows:

$$\sigma(F) = \sqrt{\frac{1}{1-N}\sum_{i=1}^{N}(F_i - F'_i)^2}$$

Herein, the F_i are the relevant load time series over a specified interval and F'_i is the time series mean.

$\sigma(F\_1)$, $\sigma(F\_2)$ is the standard deviation of the rotor thrust mechanical load on a single wind turbine. F_1 and F_2 describe the thrust force time series of one half of the rotor area, right and left side, for example the lateral sides 8_1, 8_2 illustrated in FIGS. 1 and 2. Those loads are estimated using sensors available on all wind turbines in the wind farm. The variable FA denotes the rotor thrust time history of a wake-interference free unit, for example the upwind wind turbine 1 illustrated in FIG. 1. Such wake-free units are known based on wind direction, in particular being units at the front of the row of the wind park.

The controller for repositioning is activated for a given unit when $\in\, <\|\sigma(F_2)-\sigma(F_1)\|$ The algorithm may steer the waked wind turbine unit laterally in the direction depending on the first value and the second value whichever is smaller. The load measurements for the Bayesian model is $z_{1:n}=\{\sigma_1, \sigma_2, \ldots, \sigma_n\}$ The controller inputs for the Bayesian model are the mooring line cable pay-in/pay-out lengths and wind speed.

The kinematic state for the Bayesian model is the wind turbine global position and nacelle orientation.

The SLAM algorithm may work by creating a statistical model describing the probability of wake interaction occurring on the downstream machines by treating wake area as avoidance zones. The method may be executed without the need for an explicit model or describing an environmental map of a wake region. Thus, the algorithm does not require knowledge of the wake region 4 as indicated in FIGS. 1 and 2. The wake event probability is based on a combination of prior observations and an interference algorithm to fill in the missing information. The interference algorithm can be thought of as an optimization problem where a combination of x_i, z_i:i, u_1:i is chosen in order to maximize to probability . . . occurring.

The variable z_1:i represents a time series of standard deviations of load measurements. Each $\sigma$ may be computed over a time interval of for example between 30 s and 600 s. All time series utilized in the statistical models may be discrete time series.

The initial state of the wind turbines 1, 2 is depicted in FIG. 1. The desired or target offshore position X is determined through the Bayesian model. The wind turbine 2 is then continuously moved in the general heading X. The process as performed illustrated in FIGS. 1 and 2 is performed using the method scheme illustrated in FIG. 3. Thereby, the following steps may be performed according to embodiments of the present invention:

1. Sensors on-board the FOWT measure the rotor thrust load imbalance. This controller is triggered when a load imbalance is detected: $\in_0<\|\sigma(F_1)-\sigma(F_2)\|$. This event is registered when a FOWT unit is "waked".
2. The "waked" turbine heading direction is determine based on which rotor half is loaded higher. This is done as n initial step for the algorithm to decide on a direction with the path of least resistance.
3. The motion trajectory and environment mapping are simultaneously solved using the Bayesian model. In stances where the model is undefined for a set of inputs, a maximization expectation optimization algorithm is used to infer an ideal trajectory.
4. The desired position is reached.
5. Once the designed position is reach, the standard deviation in rotor thrust loads is calculated for an unwaked wind turbine. This is determined based on wind direction and FOWT units known to be at the front of the farm row. The criterion accepted a downwind unit as "unwaked" is:

$$\|\sigma(\hat{F}_1)-\sigma(F_1)\|+\|\sigma(\hat{F}_2)-\sigma(F_2)\|\le\in_1$$

Where $\in_1$ is the acceptance threshold. Two units encounter the same loads when $\sigma(\hat{F}_1)=\sigma(F_i)$, and thus are exposed to identical atmospheric conditions regardless of location in the farm.

6. If the criterion is met, then the process of updating the FOWT position is halted, and the Bayesian probability model is updated with a "1" for the given inputs.
7. If the criterion is not accepted, then the Bayesian model is updated with a "0" for the given inputs and the process is repeated.

According to embodiments of the present invention, the following subject-matter is provided:

A wind farm including a control unit and a plurality of floating platforms, each of which is anchored to at least one anchor point and includes:

A mooring feeding system to pay-in/pay-out line at each connection point on the FOWT minimize cyclical mechanical loading on wind turbine components; and a control unit connected to sensors onboard the FOWT to measure cyclical mechanical loading on blade and nacelle acceleration.

The mooring line feeding system is a dynamic positioning system capable of automatically maintaining position and heading of the FOWT and requires:

SLAM technology and a Bayesian model to identify a position that will navigate a FOWT outside of a wake zone, thus reducing the variance in thrust loads.

a control system to track a specific desired trajectory and position;

a control system to convert the desired trajectory and position into a line pay-in/pay-out rate for each mooring fairlead in the FOWT system;

a control system to navigate and coordinate movement between FOWT units within a floating wind farm.

A dynamic positioning system including at least one mooring line pay-in/pay-out actuator suitable for changing the deployed cable length in order to change the wind turbine trajectory and position.

Communication of load time series information between FOWT units in the farm.

Additionally or alternatively to mooring lines or by mooring pay-in/pay-out adjustments, underwater azimuth thrusters may be utilized for dynamically positioning an offshore wind turbine. Additionally or alternatively to other above disclosed features, also wake steering controller may be deployed currently utilized on bottom founded offshore wind turbines. The mooring restoring force stiffness would need increase to make this approach productive.

FIG. 4 schematically illustrates a wind turbine 2 according to an embodiment of the present invention. The wind turbine 2 illustrated in FIG. 1 may for example be constructed as the wind turbine illustrated in FIG. 4. The wind turbine 2 comprises a wind turbine tower 40 which is erected at a floating platform 5 which floats on the sea 41. The floating platform 5 is connected via the mooring lines 6 to different locations 7 at the sea ground 42. On top of the wind turbine tower 40, a nacelle 45 is mounted harboring the rotor 43.

The wind turbine 2 comprises the rotor 43 at which plural rotor blades 9 are mounted. The rotor blades 9 rotate in a rotor blade plane 8. The rotor blade plane 8 can be divided into a first lateral half 8_1 and a second lateral half 8_2 of the rotor blade plane 8. At least one rotor blade 9 comprises a sensor 44 which is capable of measuring a load, for example by a strain sensor, a fibre Bragg sensor or the like. One sensor 44 is arranged at a second location 51 and another sensor 44 is arranged at a first location 49.

The wind turbine 2 further comprises an arrangement 50 for repositioning the floating offshore wind turbine 2. The arrangement 50 comprises a processor which is adapted to plural first load values 52 related to the first lateral half 8_1 of the rotor blade area 8 and to derive a first value of a variability of the first load values. Furthermore, either the sensor 44 or one or more other sensors may be capable of measuring load values related to the second half 8_2 of the rotor blade plane 8. The arrangement 50 is further configured to receive plural second load values 46 related to the second lateral half 8_2 of the rotor blade plane and to derive a second value of a variability of the second load values.

The wind turbine 2 further comprises a repositioning apparatus including actuators 47, 48 which are coupled to different mooring lines 6. Those actuators 47, 48 are capable of paying-in or paying-out the length of the mooring lines 6 in order to reposition the floating platform 5. Thereby, the arrangement 50 is communicatively coupled to the actuators 47, 48.

Sensors utilized for measuring loads may include blade load sensors and/or nacelle accelerometers. Furthermore, fibre Bragg sensors may be utilized. A Bayesian model may be utilized in the SLAM methodology. The unit position and environment mapping may be solved simultaneously using an algorithm specifically tailored for probability optimizations.

Although the present invention has been disclosed in the form of embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements.

The invention claimed is:

1. A method of repositioning a floating offshore wind turbine located at a current offshore position and having rotor blades rotating in a rotor blade plane, the method comprising:
   measuring a first value of a variability of a load related to a first location at the wind turbine;
   measuring a second value of a variability of a load related to a second location at the wind turbine;
   comparing the first value with the second value; and
   moving the wind turbine along a direction depending on the comparison;
   wherein comparing the first value with the second value comprises assessing whether an absolute value of a difference between the first value and the second value is greater than a threshold; and moving the wind turbine comprises to move the wind turbine only if the absolute value of the difference is greater than the threshold.

2. The method according to claim 1,
   wherein the first location at the wind turbine is arranged in a first lateral half of the rotor blade plane; and
   wherein the second location at the wind turbine is arranged in a second lateral half of the rotor blade plane.

3. The method according to claim 2, wherein the direction comprises a lateral direction, the method further comprising determining the lateral, or horizontal, direction:
   to point from a center area of the rotor blade plane to the first lateral half, if the first value is smaller than the second value, and
   to point from a center area of the rotor blade plane to the second lateral half, if the second value is smaller than the first value.

4. The method according to claim 1, wherein the variability of the load is indicative of a variance or a standard deviation of load sensor measurements of at least one sensor installed at the wind turbine, the sensor comprising an accelerometer and/or strain sensor and/or fibre Bragg sensor installed at nacelle and/or a rotor blade,
   wherein the variability of the load is in particular indicative of a turbulence of wind impacting at the wind turbine or at least one rotor blade.

5. The method according to claim 1, wherein the wind turbine is situated on a floating platform,
   wherein moving the wind turbine comprises controlling a positioning apparatus configured to change the offshore position of the wind turbine, the positioning apparatus comprising at least one actuator arranged at the floating platform and/or at the sea ground and/or in the sea, wherein the positioning apparatus in particular comprises at least two mooring lines being connected at one end to different locations at the floating platform and connected at another end to different locations of a sea ground, the actuator being configured to loosen and tighten the mooring lines.

6. The method according to claim 1, further comprising:
employing a first statistical model relating a wake affected state to at least one of:
the offshore position of the wind turbine;
an orientation of the nacelle of the wind turbine, the nacelle at least partly harbouring the rotor;
variabilities of load measurement values;
positioning apparatus control inputs, or pay-in and/or pay-out length of mooring lines, or time series;
a wind speed, or time series;
a wind direction.

7. The method according to claim 6, further comprising:
employing a second statistical model relating the offshore position of the wind turbine to at least one of:
a wake affected state;
an orientation of the nacelle of the wind turbine, the nacelle at least partly harbouring the rotor;
variabilities of load measurements values;
positioning apparatus control inputs, or pay-in or pay-out length of mooring lines, or time series;
a wind speed, or time series,
a wind direction,
wherein the first model and the second model have shared training data.

8. The method according to claim 7, further comprising:
determining a target offshore position based on the first and/or the second statistical model; and
moving the wind turbine to the target offshore position.

9. The method according to claim 8, further comprising:
determining a trajectory from the current offshore position to the target offshore position based on the first and/or the second statistical model; and
moving the wind turbine to the target offshore position along the determined trajectory.

10. The method according to claim 9, further comprising, when the wind turbine is at the target offshore position or at any intermediate offshore position:
measuring another first value of a variability of the load related to the first location at the wind turbine;
measuring another second value of a variability of the load related to the second location at the wind turbine;
measuring a first reference value of a variability of a load related to a first location at a reference wind turbine;
measuring a second reference value of a variability of a load related to a second location at the reference wind;
comparing the other first value with the first reference value;
comparing the other second value with the second reference value; and
determining that the wind turbine is at an acceptable offshore position, or outside a wake region, based on the reference comparisons.

11. The method according to claim 10, wherein the reference wind turbine is located not more than 5 km away from the considered wind turbine and/or wind impacting onto the reference wind turbine is unobstructed from any other wind turbine or barrier, further comprising:
updating the first and/or the second statistical model based on the reference comparisons.

12. The method according to claim 10,
wherein comparing the other first value with the first reference value includes to determine a first absolute value of a difference between the other first value and the first reference value;
wherein comparing the other second value with the second reference value comprises to determine a second absolute value of a difference between the other second value and the second reference value; and
wherein determining that the wind turbine is at an acceptable offshore position comprises to determine that a sum of the first absolute value and the second absolute value is smaller than a reference threshold.

13. An arrangement for repositioning a floating offshore wind turbine located at a current offshore position and having rotor blades rotating in a rotor blade plane area, the arrangement comprising:
a processor adapted:
to receive plural first load values related to a first location at the wind turbine and to derive a first value of a variability of the first load values;
to receive plural second load values related to a second location at the wind turbine and to derive a second value of a variability of the second load values;
to compare the first value with the second value; and
to derive control signals adapted to move the wind turbine along a direction depending on the comparison;
wherein comparing the first value with the second value comprises assessing whether an absolute value of a difference between the first value and the second value is greater than a threshold; and deriving control signals comprises deriving control signal adapted to move the wind turbine only if the absolute value of the difference is greater than the threshold.

14. A wind turbine, comprising:
a rotor at which the rotor blades are mounted and allowed to rotate in the rotor blade plane;
at least one sensor adapted to measure the plural first load values related to the first location at the wind turbine and to measure the plural second load values related to the second location at the wind turbine;
the arrangement according to claim 13 communicatively coupled to the sensor in order to receive measurement values, and
a positioning apparatus configured to change the offshore position of the wind turbine and communicatively coupled to the processor in order to receive control signals.

15. A method of repositioning a floating offshore wind turbine having rotor blades rotating in a rotor blade plane, the method comprising:
measuring a first value of a variability of a load related to a first location at the wind turbine when the wind turbine is at a first offshore position;
measuring a second value of a variability of a load related to a second location at the wind turbine when the wind turbine is at the first offshore position;
comparing the first value with the second value;
moving the wind turbine to a second offshore position depending on the comparison;
measuring a further first value of a variability of the load related to the first location at the wind turbine when the wind turbine is at the second offshore position;

measuring a further second value of a variability of the load related to the second location at the wind turbine when the wind turbine is at the second offshore position;

measuring a first reference value of a variability of a load related to a first location at a reference wind turbine;

measuring a second reference value of a variability of a load related to a second location at the reference wind turbine;

comparing the further first value with the first reference value;

comparing the further second value with the second reference value; and determining that the second offshore position is an acceptable offshore position and/or is outside a wake region based on the reference comparisons.

* * * * *